(12) United States Patent
Antonsson et al.

(10) Patent No.: US 8,703,472 B2
(45) Date of Patent: Apr. 22, 2014

(54) **STRAINS OF *LACTOBACILLUS PARACASEI***

(75) Inventors: Martin Antonsson, Svedala (SE);
Goran Molin, Lund (SE)

(73) Assignee: Probi AB, Lund (SE)

( * ) Notice: Subject to any disclaimer, the term of this patent is extended or adjusted under 35 U.S.C. 154(b) by 985 days.

(21) Appl. No.: 12/367,653

(22) Filed: Feb. 9, 2009

(65) Prior Publication Data

US 2009/0148561 A1 Jun. 11, 2009

Related U.S. Application Data

(63) Continuation of application No. 10/362,373, filed as application No. PCT/SE01/01823 on Aug. 28, 2001, now abandoned.

(30) Foreign Application Priority Data

Sep. 1, 2000 (SE) ...................................... 0003100

(51) Int. Cl.
*C12N 1/20* (2006.01)

(52) U.S. Cl.
USPC ..................... 435/252.9; 424/93.45

(58) Field of Classification Search
None
See application file for complete search history.

(56) References Cited

U.S. PATENT DOCUMENTS

2004/0052904 A1  3/2004  Antonsson et al.

FOREIGN PATENT DOCUMENTS

| CA | 2072159 | 11/1993 |
|---|---|---|
| EP | 08 61 905 | 9/1998 |
| WO | 91/17664 | 11/1991 |
| WO | 97/09448 | 3/1997 |
| WO | 99/29833 | 6/1999 |
| WO | 99/62340 | 12/1999 |
| WO | 00/53200 | 9/2000 |

OTHER PUBLICATIONS

Lynch et al. ,. Dairy Sci., 1998, vol. 82, pp. 1618-1628.*
Gardiner et al. , Applied and Environmental Microbiology, 1998, vol. 64, pp. 2192-2199.*
Gardiner et al., Applied and Environmental Microbiology, 1998, vol. 64, No. 6, pp. 2192-2199.
Midje et al., J. Agric. Food Chem., 2000, vol. 48, pp. 1630-1636.
Asensio et al., J. Agric. Food Chem., 1996, vol. 44, pp. 2919-2923.
Parra et al., Food Microbiology and Safety, 2000, vol. 65, No. 4, pp. 711-715.
Lynch et al., J. Dairy Sci., 1998, vol. 82, pp. 1618-1628.
*Who's Looking After Scottish Science; The Hannah Research Institute*, 1-8 (printed on Feb. 27, 2012).

* cited by examiner

*Primary Examiner* — Irene Marx
(74) *Attorney, Agent, or Firm* — Buchanan Ingersoll & Rooney P.C.

(57) ABSTRACT

New strains of *Lactobacillus paracasei* which can be used as probiotics in dairy products and which are characterized in surviving the gastrointestinal passage and giving a palatable cheese product when used as an adjunct in cheese manufacturing. The invention especially refers to the new strains *Lactobacillus paracasei* 8700:2, DSM 13434, and *Lactobacillus paracasei* 02A, DSM 13432. The invention also refers to dairy food products, such as cheese, containing said strains.

5 Claims, 3 Drawing Sheets

REA-profile of strain DSM 13434

REA-profile of strain DSM 13432

STRAINS OF *LACTOBACILLUS PARACASEI*

CROSS-REFERENCE TO RELATED APPLICATIONS

This application is a continuation of U.S. patent application Ser. No. 10/362,373, filed on Sep. 29, 2003, now abandoned, which is a U.S. national stage application pursuant to 35 U.S.C. §371 of International Patent Application PCT/SE01/01823, filed on Aug. 28, 2001, and published as WO 02/018542 on Mar. 7, 2002, which claims priority to Swedish Patent Application 0003100-5, filed on Sep. 1, 2000.

The present invention refers to new strains of *Lactobacillus paracasei* which can be used for the manufacture of fermented dairy products, especially probiotic cheese.

BACKGROUND OF THE INVENTION

Swedish cheese is made from pasteurized cows milk which is fermented by a starter culture of lactic acid bacteria. The acidified milk is curdled by rennet (chymosin) and the coagulated milk is cut and stirred. The mixture of whey and cheese grains is gently heated. The whey is separated and the cheese grains pressed to a cheese which is salted and ripened; the order of whey separation and pressing depends on the cheese variety. During the ripening a secondary flora of mainly lactic acid bacteria is growing spontaneously.

Swedish hard and semi-hard cheese will during the ripening be dominated by a spontaneously growing secondary microflora, often referred to as non-starter lactic acid bacteria, NSLAB. This spontaneous flora succeed the added starter culture and grow under the selective conditions of a maturing cheese. NSLAB are thought to enter the dairy plant either with the raw milk after surviving the pasteurization or with other ingredients used for the cheese making. The NSLAB most commonly found in Swedish and Norwegian cheese belong to the genus *Lactobacillus* and especially the species *Lactobacillus paracasei*, see Lindberg, A.-M., et al., Bacterial flora of Norwegian and Swedish semi-hard cheese after ripening, with special reference to *Lactobacillus*, Netherlands Milk & Dairy Journal 50 (1996) 563-572. NSLAB start to grow after a few days of ripening and reach levels of about $10^6$-$10^7$ cfu/g after one month of ripening and this level is maintained for at least five months. Cheddar cheese show the same development of NSLAB dominated by lactobacilli. Examples of species reported from Cheddar are *Lactobacillus casei, Lactobacillus plantarum* and *Lactobacillus brevis*, but usually the dominating species are *Lactobacillus casei* or *Lactobacillus paracasei*. As the NSLAB is not controlled, it is plausible that some of the variations in cheese quality is due to the variability in the composition of the NSLAB. In order to control the process of ripening and the growth of the spontaneous flora of NSLAB, pure cultures of strains of for instance *Lactobacillus* have been used as adjuncts in cheese manufacturing. Said adjuncts in general might have an effect on the aroma and flavour of the cheese product; an effect which is not predictable but has to be tested by trial and error.

Probiotic microorganisms in dairy products have been the subject for intense research during the last decade. The potential health-promoting effects of dairy products which incorporate probiotic organisms, such as *Lactobacillus* and *Bifidobacterium* spp., has stimulated said research. Probiotic bacteria are described as "a live microbial feed supplement which beneficially affects the host animal by improving its microbial balance" which upon digestion in certain numbers exert health benefits, Fuller, R., Probiotics in man and animal, Journal of applied Bacteriology, 66 (1989) 365-378. Desirable traits for selection of functional probiotics are summarized and described by Klaenhammer, T. R., et al., Selection and design of probiotics, International Journal of Food Microbiology 50 (1999) 45-47. The selection criteria are said to fall into four basic categories, that is appropriateness such as nontoxicity, technological suitability such as viability, competiveness that is capability to survive in the gut, performance and functionality. Understanding the mechanisms of how these criteria impact in vivo functionality will present a major challenge in the future.

PRIOR ART

Previous studies have demonstrated that bifidobacteria as well as a number of probiotic *Lactobacillus* strains can survive well in hard cheeses, such as Cheddar cheese and Gouda cheese.

Gomes, A. M., et al., Incorporation and survival of *Bifidobacterium* sp. strain Bo and *Lactobacillus acidophilus* strain Ki in a cheese product, Netherlands Milk & Dairy Journal 49 (1995) 71-95, discloses the manufacture of a probiotic Gouda cheese using a combination of a strain of *Bifidobacterium* and a strain of *L. acidophilus* as a starter. It was found that both species survived relatively good, but that the sensory properties were negatively affected.

Dinkar et al., Growth and viability of *Bifodobacterium bifidum* in Cheddar cheese, J Dairy Sci 77:2854-2864, 1994, discloses the incorporation of *Bifidobacterium bifidum* into Cheddar. A good viability ($10^7$ cfu/g) without negative effects on the cheese quality after 6 months of ripening was obtained if the bacteria were added as an adjunct at a later stage of cheese making, such as milling or salting. This study was followed by a trial were the performance of a number of probiotic *Lactobacillus* strains, *L. salivarius* and *L. paracasei*, were studied in Cheddar over a period of 8 months of ripening; Gardiner et al., Development of a probiotic Cheddar cheese containing human-derived *Lactobacillus paracasei* strains, Applied and Environmental Microbiology, 292-2199, June 1998. It was concluded that the probiotic *L. paracasei* strains were particularly suitable as adjuncts as they grew to high numbers in the cheese and influenced the proteolysis but not the sensory properties.

DESCRIPTION OT THE DRAWINGS

DESCRIPTION OF THE INVENTION

The present invention refers to new probiotic strains of *Lactobacillus paracasei* which can be used as adjuncts in the production of cheese, which strains have advantageous survival properties in cheese as well as the ability to give the cheese a good flavour.

The invention especially refers to a strain of *Lactobacillus paracasei* which can be used as probiotics in diary products, and which is characterized in surviving the gastro-intestinal passage and giving a palatable cheese product when used as an adjunct in the production of cheese.

Figure 1:
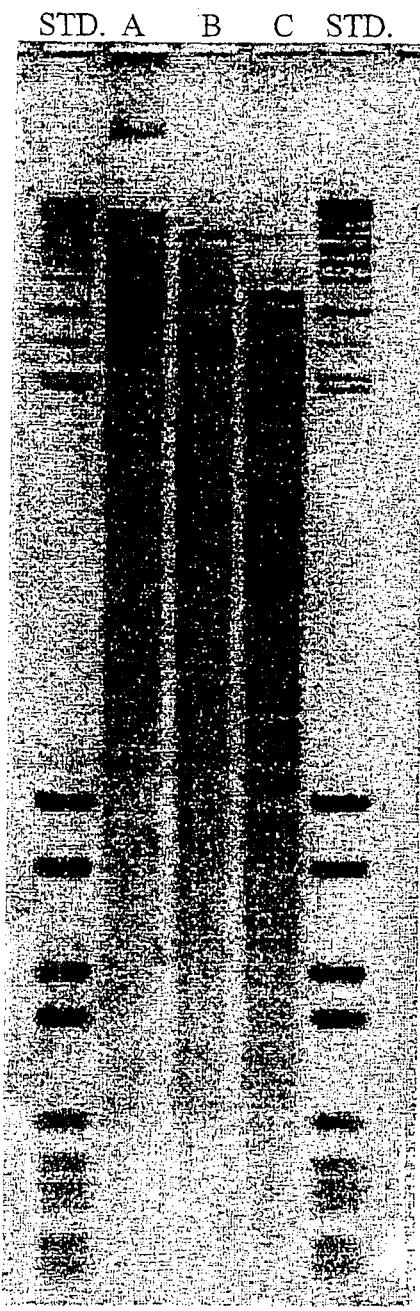
FIG. 1 is the image of the REA-profile of the strain *Lactobacillus paracasei* 8700:2, DSM 13434.

According to a preferred aspect the invention refers to the strain *Lactobacillus paracasei* 8700:2, which has been deposited with the DSMZ-Deutsche Sammlung von Mikroorganismen und Zellkulturen GmbH, Mascheroder Weg 1b, 38124 Braunschweig, Germany, on Apr. 10, 2000, and has been given the accession number DSM 13434, or a variant thereof. FIG. 1 shows the REA-profile of this strain, that is the Restriction Endonuclease Analysis profile obtained from the total chromosomal DNA after cutting with the restriction enzymes Hind III (lane C), Cla I (lane B) and Eco RI (lane A). STD stand for a size marker, which is a combination of High Molecular Marker (Life Technologies) and DNA Molecular Weight Marker VI (Rouche Molecular Biochemicals, Boehringer Mannheim).

Figure 2:
FIG. 2 is the image of the REA-profile of the strain *Lactobacillus paracasei* 02A, DSM 13432.

According to another preferred aspect the invention refers to the strain *Lactobacillus paracasei* 02A, which has been deposited with the DSMZ-Deutsche Sammlung von Mikroorganismen und Zellkulturen GmbH, Mascheroder Weg 1b, 38124 Braunschweig, Germany, on Apr. 10, 2000, and has been given the accession number DSM 13432, or a variant thereof. FIG. 2 shows the REA-profile of this strain, that is the Restriction Endonuclease Analysis profile obtained from the total chromosomal DNA after cutting with the restriction enzymes Hind III (lane C), Cla I (lane B) and Eco RI (lane A). STD stands for a size marker, which is a combination of High Molecular Marker (Life Technologies) and DNA Molecular Weight Marker VI (Rouche Molecular Biochemicals, Boehringer Mannheim).

The REA-analysis was performed according to Johansson et al., International Journal of Systematic Bacteriology (1995) 10, 670-675.

Figure 3:
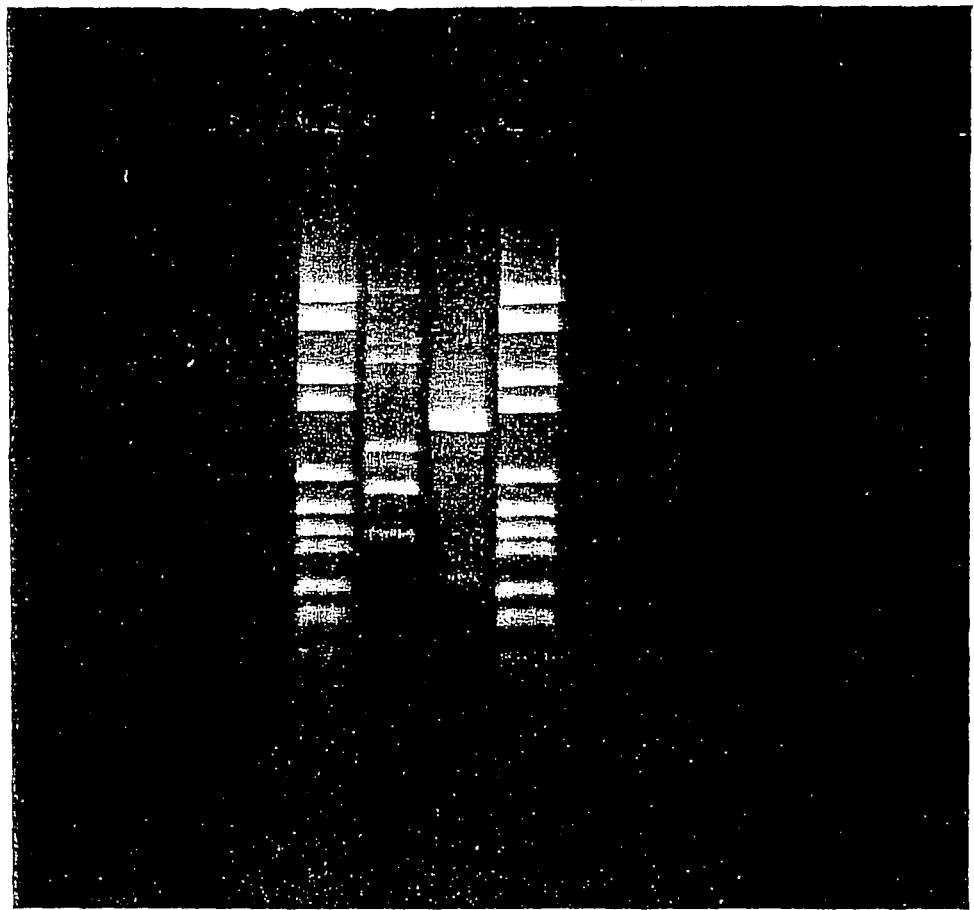
FIG. 3 is a photo of the RAPD-profiles of the two strains *L. paracasei* 8700:2 and 02A.

FIG. 3 shows the RAPD-profiles of strain 02A (lane 2) and strain 8700:2 (lane 3). Lanes 1 and 4 are DNA Molecular Weight Marker VI (Rouche Molecular Biochemicals, Boehringer Mannheim). The RAPD-analysis was performed as described in Material and methods, below.

The new strains of the invention can be used as a probiotic in any dairy food product, such as fermented dairy products, yogurt and ice-cream, spread, fresh cheese, hard and semi-hard cheeses manufactured with calf-rennet and with a fat content of 5-50%, soft cheese and quarge and quarg based products with a fat content of 0.1-40%, as well as keso with or without fermented dressing or live bacteria in the curd.

A preferred use of a strain according to the invention is as an adjunct in the manufacture of cheese.

The invention also refers to a dairy food product which contains one or more of the new strains of the invention. The content of the probiotic strain in the food product should be $10^6$-$10^9$ cfu/g, preferably above $10^7$.

According to a preferred aspect the invention refers to a hard or semi-hard cheese with improved flavour, which contains the strains *Lactobacillus paracasei* 8700:2, DSM 13434; or to a hard or semi-hard cheese with improved flavour, which contains the strain *Lactobacillus paracasei* 02A, DSM 13432.

According to another aspect the invention also refers to a yogurt which contains the strain *Lactobacillus paracasei* 8700:2, DSM 13434, or *Lactobacillus paracasei* 02A, DSM 13432, in admixture with conventional yogurt cultures.

EXEMPLIFICATION

Screening Test of Probiotic Strains in a Cheese Model 15 different *Lactobacillus* strains of intestinal origin (*Lactobacillus rhamnosus* 11 strains, *Lactobacillus paracasei* 3 strains and *Lactobacillus plantarum* 1 strain), were tested in a screening trial in a cheese model monitoring the ability to grow and survive in cheese and the influence on cheese flavour. The different strains had been obtained from human intestines using the method described in Molin, G., et al., Numerical taxonomy of *Lactobacillus* spp. associated with healthy and diseased mucosa of the human intestines, Journal of Applied Bacteriology 74 (1993) 314-323.

As a result of this test 4 of the strains were chosen for further studies; the strains are presented in Table 1 below.

TABLE 1

| Strain | Organism |
|---|---|
| 02A | *L. paracasei* |
| 04C | *L. plantarum* |
| 8700:2 | *L. paracasei* |
| 8589:2 | *L. paracasei* |

Screening Test of Probiotic Strains in 30+ Round-Eyed Cheese

This study investigates the performance of three strains of *Lactobacillus paracasei* and one *Lactobacillus plantarum* strain, all isolated from human intestinal mucosa, as adjuncts in a round-eyed cheese with at least 30% fat in dry matter.

The test strains are presented in Table 1 above.

Material and Methods

Cheese Manufacture

Cheeses were manufactured in a 400 l vat, according to a standard protocol, from pasteurized (73° C., 15 s) cow's milk (Skånemejerier, Hörby, Sweden). The cheeses manufactured were semi-hard, round-eyed with 30% fat in dry matter. The cheese milk was inoculated with $10^6$ cfu/ml of the test strains. The test strains were added to the milk after (30 min) inoculation with the lactic starter culture, from thawed freezing buffer. Each batch yielded four cheeses of approximately 10 kg, out of which three were ripened at 12° C. and one was initially ripened at 16° C. for 14 days and thereafter at 12° C. The cheeses were ripened in plastic foil. The cheesemaking was performed in four replicates. Four batches were made each week, three batches with different adjuncts and one control batch, without adjunct. The manufacturing order was randomised for each week. Totally 22 batches were manufactured, 6 control batches and 4 batches with each of the 4 adjunct cultures.

Cheese Analysis

Two separate batches produced with different adjuncts and two control batches were sampled after 5 months of ripening, 1 cheese from each batch. The remaining 4 control batches and duplicate batches with different adjuncts were sampled after 6 months of ripening (2 cheeses from each batch ripened at different initial temperatures). The cheeses were sampled for their sensory properties, microbiological properties and physico-chemical properties.

Microbiological Sampling of Cheese

A sample of 10 g was aseptically collected from the centre of the cheese and homogenised with 90 ml 2% sodium citrate solution in a Stomacher (Seward Medical Limited, London SE1 1PP, UK) for 2.5 min. After conventional dilution and plating, total aerobic and anaerobic viable counts were done on Brain Heart Infusion agar (BHI; Difco, Sparks, USA) incubated at 28° C. for 4 days. Viable count of lactobacilli were analysed on Rogosa agar (Merck, Darmstadt, Germany) incubated anaerobically at 28° C. for 4 days.

Isolation of Microorganisms from Cheese

Seven colonies were randomly picked from each sample. Two were picked from the total viable counts (BHI agar) and three from the selective viable count of lactobacilli (Rogosa agar). Countable plates with no less than 20 colonies were used.

Microbiological Analysis
REA-Analysis

Chromosomal DNAs were prepared for the Restriction Endonuclease Analysis (REA) according to the protocol of Johansson et al., 1995, see above. The chromosomal DNA was separated from covalently closed circular plasmid DNA (most of the plasmid DNA) by dye buoyant density centrifugation in a CsCl gradient with ethidium bromide. Some linear and open circular forms of plasmid DNA may still be present in the preparations, but only cintributing marginally to the final result. The concentration of the chromosomal DNA was monitored in a fluorometer (Model TKO 100, Hoefer Scientific Instruments, San Francisco, USA). DNA (0.75 mg) was separately digested at 37° C. for 4 h with 10 units of HindIII, CLAI or ECORI (Boehringer). Electrophoresis and scanning of gels was performed as described by Johansson et al. Submerged horizontal 0.9% agarose slab gels in size of 150-235 mm were used. An amount of 0.2 mg of a high molecular weight DNA marker (containing DNA fragments of molecular weights from 8.5 to 48.5 kb (Bethesda Research Laboratories, BRL) together with 0.5 mg of DNA molecular weight marker VI containing DNA fragments of molecular weights from 0.2 to 2.2 kb (Boehringer Mannheim) were used as standards. Gels were run at a constant voltage of 40 V for 18 h at 8.5° C. The buffer was recirculated during the running period. Thereafter the gels were stained for 20 minutes in ethidium bromide (2 mg/ml), destined in distilled water, visualized at 302 nm with a UV transluminator (UVP Inc., San-Gabriel, USA) and photographed. This way of running the gel electrophoresis gives well-distributed and relatively well-separated bands down to a molecular weight of about 1.8 kb. REA-patterns on photonegatives were scanned into a computer with a flatbed scanner at a resolution of 200 dpi. The gel images were than converted to BioNumerics format (Applied Maths, Kortrijk, Belgium) Normalization and all further analysis of the gels was done in BioNumerics 1.0. The gel traces were analyzed with Pearson product moment correlation coefficient and the unweighted pair group method by arithmetic averages (UPGMA). The data from the three cleavages, that is by HIND III, CLA I and Eco RI, were combined for each strain using BioNumerics 1.0.

RAPD-Analysis

All isolates were typed by the method of Randomly Amplified Polymorphic DNA, that is RAPD (Quednau et al., 1998, Current Microbiology, 36, 332-336) Crude cell extracts were prepared from over night cultures incubated at 28° C. in 1 ml BHI for isolates from the BHI agar plates and in 1 ml *Lactobacillus* carrying medium, LCM, for isolates from the Rogosa agar plates. The cells of pure culture were washed twice in 1 ml sterile Milli-Q® water (Millipore S. A., Molsheim, France), and disrupted in an Eppendorf tube with glass beads, 2 mm in diameter, using an Eppendorf Mixer (5432; Eppendorf, Hamburg, Germany). The primer used had the sequence 5'-ACGCGCCCT-3' with a concentration in the reaction mixture of 15 mM. The RAPD-procedure resulted in a suitable number of distinct bands on the gels for the presently typed lactobacilli, as it previously has been proved to do for *Lactobacillus plantarum* (Johansson, M. L., et al., Randomly amplified polymorphic DNA (RAPD) for typing of *Lactobacillus plantarum* strains, Letters in Applied Microbiology, 21 (1995) 155-159).

The band patterns of the gels were analysed with Pearson product moment correlation Coefficient® and the Unweighted Pair Group Method with Arithmetic averages (UPGMA; Romesburg, 1984) by using Gel Compar™ 4.2 (Applied Maths, Kortrijk, Belgium). The computerised cluster analysis of the RAPD-patterns was combined with a visual comparison.

Sensory Assessment

The cheeses were graded after 5 months by 7 graders (6 expert graders and 1 member of the staff at the Department of Food technology, Lund University), on a hedonic scale (translated into a 0-10 scale after analysis) considering the number of attributes, (quality of: surface, smell, initial texture, secondary texture, flavour and intensity of: smell, flavour, off-flavour) and overall quality. After 6 months the cheeses were graded by 4 expert graders, on a hedonic scale considering surface-, texture-, smell-, flavour- and overall-quality and the intensity of 11 connected attributes. The cheeses were tempered to 16° C. and marked with a random 3 digit number and served in a random order.

Results
Cheese Manufacture

The pH of the cheeses during manufacture were similar in all the test groups. The composition of the cheeses varied as expected between the test groups, due to the difficulties in manufacturing cheese in this scale.

Microbiological Analysis of Cheese

In cheeses sampled after 5 months of ripening, cheeses manufactured with adjunct had about 1 Lg cfu/g higher viable counts than the reference cheeses. The values are given in the following Table 2.

TABLE 2

Bacterial viable counts in cheese after 5 months ripening

| Cheese | Viable counts, Lg(cfu/g cheese) | | |
|---|---|---|---|
|  | total aerobic | total anaerobic | *Lactobacillus* |
| Control | 6.85 ∓ 0.33 | 7.27 ∓ 0.02 | 6.81 ∓ 0.00 |
| +04C | 7.50 ∓ 0.25 | 7.74 ∓ 0.27 | 7.42 ∓ 0.02 |
| +8589:2 | 8.20 ∓ 0.01 | 8.20 ∓ 0.02 | 7.62 ∓ 0.00 |
| +8700:2 | 7.98 ∓ 0.04 | 7.56 ∓ 0.50 | 7.49 ∓ 0.05 |
| +02A | 7.72 ∓ 0.04 | 7.65 ∓ 0.43 | 7.58 ∓ 0.00 |

The isolates from all of the sampled cheeses after 5 months of ripening (10 cheeses, 70 isolates) were classified into 12 different RAPD-types. The isolates from the control cheese were classified into 7 different RAPD-types while the isolates from cheeses manufactured with adjunct 04C were of 5 different RAPD-types and the isolates from cheeses manufactured with adjunct 02A were of 4 different RAPD-types. The isolates from cheeses manufactured with adjuncts 8700:2 and 8589:2 were of 3 different RAPD-types, respectively. All cheeses had isolates of one RAPD-type in common.

All of the used adjunct cultures were found in the corresponding duplicate samples of cheese, after 5 months of ripening. The adjunct cultures 04C, 8589:2 and 02A were reisolated from *Lactobacillus*-selective agar only (04C: 2 out of 6 isolates; 8589:2: 3 out of 6 isolates; 02A 4 out of 6 isolates). In one control cheese, one isolate of the same RAPD-type as 04C was found and in the other control cheese, one isolate of the same RAPD-type as 02A was found. Adjunct 8700:2 was reisolated from total count agar (2 out of 8 isolates) and *Lactobacillus*-selective agar (6 out of 6 isolates).

In cheeses sampled after 6 months of ripening the total viable counts for all test groups were similar (8.0-8.4 Lg (cfu/g cheese)) in cheeses ripened at 12° C. In cheeses initially ripened at 16° C. the total viable counts were generally lower than in cheeses ripened at 12° C., especially in the control cheeses (7.4-7.5 Lg (cfu/g cheese)). The selective counts of lactobacilli in cheeses ripened at 12° C. were generally higher in cheeses manufactured with adjuncts (7.6-7.8 Lg (cfu/g cheese)) than in the control (7.3 Lg (cfu/g cheese)). The selective count of lactobacilli after 6 months of ripening was not influenced by the increased initial ripening temperature.

Sensory Assessment

After 5 months of ripening, the control cheeses had the significantly lowest scores for texture (initial and secondary) compared to cheeses manufactured with adjuncts. The surface had significantly lower scores in the control and cheese manufactured with adjunct 8700:2 compared to cheeses manufactured with adjuncts 8589:2 and 02A. Cheeses manufactured with adjuncts 8700:2 and 02A had significantly higher scores for flavour quality and overall quality compared to the control cheeses. Among the cheeses manufactured with adjunct culture, cheeses manufactured with 8700:2 had the highest score for overall quality and the lowest score for off-flavour intensity. Cheeses manufactured with 02A had the highest scores for flavour quality and intensity. All analysed cheeses received very similar scores for the quality and intensity of smell (data not shown).

In Table 3 below the pH during manufacture, the fat in dry matter and moisture in non-fat solids for one cheese from 2 batches of each test-group (mean±standard deviation) is shown. The scale for the sensory assessment are 1=bad quality, low intensity; 10=good quality, high intensity; mean±standard deviation.

After 6 months of ripening no significant differences were found between cheeses from different test groups. The main trends seen were though, that the increased initial ripening temperature decreased the texture quality and improved the flavour, especially for cheeses produced with adjuncts.

randomly divided into three groups: 1) consumed the control cheese without added adjuncts, 2) consumed cheese inoculated with 8700:2 and 3) consumed cheese inoculated with 02A. Group 1 consisted of 8 volunteers (4 males and 4 females aged 43-51 years), group 2 consisted of 10 volunteers (5 males and 5 females aged 25-55 years) and group 3 consisted of 11 volunteers (6 males and 5 females aged 26-60 years). The study was pursued for 5 weeks. During weeks 3 and 4 150 g of the cheese was administered daily, which corresponds to a daily dose of the test strain of >0.5-109 cfu. During the study, persons were forbidden to eat products containing probiotic bacteria or antibiotics. Faecal samples were collected before the start of administration (week 2), after 2 weeks of administration (week 4) and 1 week after the end of administration (week 5).

Isolation of Micro-Organisms from Faeces

After conventional dilution and plating of faeces, viable counts of lactobacilli were analysed on Rogosa agar incubated anaerobically at 37° C. for 3 days. Three colonies were randomly picked from each sample for typing. Countable plates with no less then 20 colonies were used.

Typing of Isolates

All isolates were typed by the method of Randomly Amplified Polymorphic DNA (RAPD; Quednau et al., 1998, supra).

Reisolation

RAPD patterns of isolates from cheeses manufactured with adjuncts was compared with the RAPD pattern of the adjunct and of isolates from the reference cheeses. If the isolates from the cheese with adjunct were of the same RAPD-type as the adjunct, the adjunct was considered to be reisolated.

RAPD-patterns from isolates from faeces from each person was compared with the RAPD-pattern of the adjunct, isolates from cheeses made with this adjunct and isolates from reference cheeses. If isolates of the same RAPD-type as

TABLE 3

Cheese manufactured with different adjuncts sensory evaluated after 5 months of ripening

|  | Control[1] | 04C | 8589:2 | 02A | 8700:1 |
|---|---|---|---|---|---|
| PH after pressing | 6.01 ± 0.05 | 6.04 ± 0.04 | 5.91 ± 0.02 | 5.93 ± 0.06 | 6.01 ± 0.05 |
| PH after salting | 5.39 ± 0.00 | 5.40 ± 0.00 | 5.36 ± 0.03 | 5.36 ± 0.02 | 5.36 ± 0.03 |
| Fat in Dry Matter (%) | 34.25 ± 0.60 | 33.65 ± 0.60 | 32.30 ± 0.70 | 31.95 ± 0.17 | 33.20 ± 0.63 |
| Moisture in Non Fat Solids (%) | 63.40 ± 0.07 | 60.15 ± 0.11 | 58.65 ± 0.74 | 60.05 ± 0.32 | 59.80 ± 0.70 |
| Surface[2] | 3.42 ± 0.50*[a] | 5.69 ± 1.76 | 6.72 ± 0.83*[b] | 7.20 ± 0.94*[b] | 4.09 ± 0.60*[a] |
| Initial Texture[2] | 3.98 ± 0.43*[c] | 7.04 ± 0.98*[d] | 6.66 ± 0.88*[d] | 7.16 ± 0.81*[d] | 6.86 ± 0.89*[d] |
| Secondary Texture[2] | 3.91 ± 0.81*[e] | 6.15 ± 0.85*[f] | 5.80 ± 0.74*[f] | 6.72 ± 0.79*[f] | 6.47 ± 0.81*[f] |
| Flavour Quality[2] | 4.25 ± 0.86*[g] | 5.39 ± 0.71 | 5.45 ± 0.67 | 6.19 ± 0.61*[h] | 6.44 ± 0.63*[h] |
| Flavour Intensity | 4.98 ± 0.83 | 5.84 ± 0.84 | 5.77 ± 0.62 | 5.96 ± 0.52 | 6.08 ± 0.69 |
| Off-flavour Intensity | 3.52 ± 1.38[3] | 2.16 ± 0.92[4] | 2.70 ± 0.91[4] | 2.08 ± 0.65[4] | 1.58 ± 0.81[4] |
| Overall Quality[2] | 3.78 ± 0.86*[i] | 5.34 ± 0.65 | 5.06 ± 0.74 | 6.03 ± 0.49*[j] | 6.49 ± 0.60*[j] |

[1]No adjunct were added
[2]significant differences (P = 0.05) between groups indicated with different letters.
[3]acid and bitter
[4]bitter Test of the Probiotic Properties Also, the ability of the strains to survive intestinal passage when delivered in a cheese was controlled and compared with the spontaneously grown secondary microflora.

Administration Study

Oral Administration

Cheeses inoculated with strains 02A and 8700:2 were selected for the administration study. This selection was based on superior flavour of inoculated cheeses and the test strains ability to grow and survive in the cheese during ripening. The cultures were present in the cheese with more than $10^7$ cfu/g cheese. Volunteers for oral administration were the adjunct were found in faeces after administration of cheese, and not prior to the administration, it was concluded that the adjunct survived intestinal passage. Also, if isolates of the same RAPD-type as the adjunct were found in faeces 1 week after administration of cheese, and not prior to the administration, it was concluded that the adjunct colonised the human bowel.

Statistical Analyses

Analyses of variation and significant differences in viable counts and sensory scores were made by calculating confidence intervals using the t-distribution. A statistical evaluation of the significance of differences in the viable counts in faeces at the three sampling times was performed with the Wilcoxon rank sum test using SPSS 6.0 (SPSS inc., Chicago, USA)

Result of Oral Administration

Strain 02A were found in the faeces of 6 out of 11 volunteers, directly after the end of administration. The corresponding figure for strain 8700:2 were 10 out of 10 volunteers. Neither 02A nor 8700:2 were found in faeces of any of the volunteers in these two groups 1 week after ended administration. None of the spontaneously occurring RAPD-types in the control cheeses or in cheeses manufactured with adjunct were found in faeces of the volunteers. Though, isolates of the same RAPD-type as 02A were found in the faeces of 2 volunteers that was administered the control cheese, directly after the end of administration. Also, isolates of the same RAPD-type as 04C were found, 1 week after the end of administration, in the faeces of 2 volunteers. These 2 volunteers were administered control cheese or cheese manufactured with adjunct 02A. The viable counts of lactobacilli in faeces increased in all groups after the cheese consumption. The increase was statistically significant for the groups eating cheese containing adjunct culture. After the end of administration, the viable counts of lactobacilli decreased for the groups eating cheeses containing adjunct culture, significant for group 3, while it increased for the group eating the control cheese.

The following Table 4 shows the selective count of lactobacilli for the three groups in the study

TABLE 4

| Group after | 1 Control cheese | 2 Cheese + 8700:2 | 3 Cheese + 02A |
| --- | --- | --- | --- |
| 2 weeks | 5.81 ∓ 0.74 | 4.87 ∓ 0.38 | 5.94 ∓ 0.48 |
| 4 weeks | 6.08 ∓ 0.60 | 6.72 ∓ 0.80 | 6.64 ∓ 0.46 |
| 5 weeks | 6.97 ∓ 0.74 | 5.59 ∓ 0.92 | 5.74 ∓ 0.54 |

CONCLUSION

The experiments above have shown that the two strains *Lactobacillus paracasei* 8700:2, DSM 13434, and *Lactobacillus paracasei* 02A, DSM 13432, perform well as adjunct cultures for manufacturing of cheese and could be reisolated from the cheese after 5 months of ripening. The strains also have a positive effect on the sensory properties, which means that they were able to dominate over the spontaneously growing secondary microflora.

The administration study has showed that the two strains seem to fulfil the demand of competitiveness as surviving the gastrointestinal passage and therefor fulfil the selection criteria for a potential probiotic strain.

The invention claimed is:

1. An isolated strain of *Lactobacillus paracasei*, wherein
   the strain survives the gastrointestinal passage and gives a palatable cheese product when used as an adjunct in the production of cheese, and
   the strain is *Lactobacillus paracasei* 8700:2, DSM 13434.

2. The isolated strain according to claim 1, for use as an adjunct in the manufacture of cheese.

3. A dairy food product comprising an isolated strain according to claim 1 in an amount of $10^6$-$10^9$ cfu/g.

4. The product according to claim 3, which is a hard or semi-hard cheese with improved flavour.

5. The product according to claim 3, which is a yogurt, wherein the product comprises the strain *Lactobacillus paracasei* 8700:2, DSM 13434, in admixture with conventional yogurt cultures.

* * * * *